United States Patent [19]

Butter et al.

[11] 3,965,209

[45] June 22, 1976

[54] SELECTIVE PRODUCTION OF PARA-XYLENE

[75] Inventors: Stephen Allan Butter, East Windsor; Lewis Brewster Young, Kendall Park, both of N.J.

[73] Assignee: Mobil Oil Corporation, New York, N.Y.

[22] Filed: Jan. 6, 1975

[21] Appl. No.: 538,665

[52] U.S. Cl. ................. 260/671 M; 208/DIG. 2; 260/671 C; 260/671 R
[51] Int. Cl.$^2$ ................. C07C 3/52; C07C 15/08
[58] Field of Search ....... 260/671 R, 671 C, 671 M; 208/DIG. 2

[56] References Cited
UNITED STATES PATENTS

| | | | |
|---|---|---|---|
| 3,437,587 | 4/1969 | Ellert et al. | 208/DIG. 2 |
| 3,669,903 | 6/1972 | Bourquet et al. | 260/671 |
| 3,728,408 | 4/1973 | Tobias | 260/671 |
| 3,751,506 | 8/1973 | Burress | 260/671 |
| 3,755,483 | 8/1973 | Burress | 260/671 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Process for the selective production of para-xylene by methylation of toluene in the presence of a catalyst comprising a crystalline aluminosilicate zeolite, said zeolite having a silica to alumina ratio of at least about 12 and a constraint index, as hereinafter defined, within the approximate range of 1 to 12 which catalyst has undergone prior treatment with steam to reduce the alpha value thereof to less than about 500 and preferably within the range of less than about 20 but greater than zero.

12 Claims, No Drawings

SELECTIVE PRODUCTION OF PARA-XYLENE

BACKGROUND OF THE INVENTION

1. Field of the Invention

This invention relates to a process for the selective production of para-xylene by catalytic methylation of toluene in the presence of a steam treated crystalline aluminosilicate catalyst.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275°C., with the maximum yield of para-xylene in the mixture of xylenes, i.e. about 50 percent of the xylene product mixture, being observed at 225°C. Higher temperatures, were reported to result in an increase in the yield of meta-xylene and a decrease in production of para and ortho-xylenes.

While the above-noted prior art is considered of interest in connection with the subject matter of the present invention, the methylation process described herein utilizing a catalyst of a crystalline aluminosilicate zeolite, said zeolite having a silica/alumina ratio of at least about 12 and a constraint index of from 1 to 12, which catalyst has undergone prior steam treatment to achieve unexpectedly high selective production of para-xylene has not, insofar as is known, been heretofore described.

Of the xylene isomers, e.g. ortho-, meta- and para-xylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and miltistage refrigeration steps. Such process, as will be realized, has involved high operation costs and has a limited yield.

SUMMARY OF THE INVENTION

In accordance with the present invention, there has been discovered a process for selectively producing para-xylene in preference to meta- or ortho-xylene by reaction of toluene with a methylating agent in the presence of a catalyst comprising a crystalline aluminosilicate zeolite, said zeolite having a silica to alumina ratio of at least about 12 and a constraint index of from 1 to 12, which catalyst has undergone prior steam treatment to reduce the activity thereof, as expressed in terms of alpha, to less than about 500 and preferably in the range of less than about 20 but greater than zero.

Compared to a conventional thermodynamic equilibrium xylene mixture in which the para:meta: ortho is approximately 1:2:1, the process described herein affords a xylene product having a para:meta:ortho ratio of about 65:1:1 or higher. The improved para-xylene yield reduces the cost of separation of para-xylene from its isomer which is the most expensive step in the current method employed for producing para-xylene.

The present process comprises methylation of toluene preferably by reaction of the latter with methanol in the presence of a particular modified crystalline aluminosilicate catalyst. The catalyst employed is a crystalline aluminosilicate zeolite having a silica to alumina ratio of at least about 12 and a constraint index of from 1 to 12 which has been modified by steam treatment to reduce the alpha value thereof to less than about 500. Steam treatment is effected by contact of the specified crystalline aluminosilicate zeolite with an atmosphere containing from about 5 to about 100 percent steam at temperature of from about 250° to about 1000°C and under pressures ranging from subatmospheric to several hundred atmospheres. The treatment may be accomplished in an atmosphere of 100 percent steam or in an atmosphere consisting of steam and a gas which is substantially inert to the aluminosilicate. The time of treatment to achieve the desired reduction in activity will depend on the steam content of the treating atmosphere and the temperature and pressure, as well as on the nature of the particular zeolite undergoing treatment, but will generally be for a period of at least about one-half hour and may extend up to 100 hours or longer.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many evironments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalyst useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000°F. for at least 15 minutes. The catalyst is then flushed with helium and the temperature adjusted between 550°to and 950°F. to give an overall conversion between 10 and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
| --- | --- |
| ZSM-5 | 8.3 |
| ZSM-11 | 8.7 |
| ZSM-12 | 2 |
| ZSM-21 | 4.5 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950°F., with accompanying conversion between 10 and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550°F. to 950°F., the constraint index will have a value for any given zeolite of interest herein within the approximate range of 1 to 12.

The class of zeolites defined herein is exemplified by ZSM-5, ZSM-11, ZSM-12, ZSM-21, ZSM-35 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. Application Ser. No. 560,412, filed Mar. 20, 1975. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)\ M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and $x$ is from greater than 8 to about 50.

The synthetic ZSM-21 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11,33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-21 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-21 (after calcination at 600°C.) is less than 10, whereas that ratio for the natural ferrierite is substantially greater than 10, for example, as high as 34 or higher.

Zeolite ZSM-21 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05 14 0.5 | 0.07–0.49 |
| H₂O/OH⁻ | 41–500 | 100≅250 |
| SiO₂/Al₂O₃ | 8.8–200 | 12–60 | wherein R is an organic nitrogen-containing cation derived from a 2-(hydroxyalkyl)trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400°C. for a period of time of from about 6 hours to about 100 days. A more preferred temperature range is from about 150° to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230°F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

(0.3–2.5)R₂O : (0–0.8)M₂O : Al₂O₃ : > 8 SiO₂ 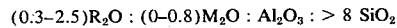

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R₂O : (0.0.6) M₂O : Al₂O₃ : xSiO₂ 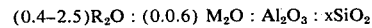

wherein R is an organic nitrogen-containing cation derived from ethylenediamine or pyrrolidine, M is an alkali metal, especially sodium, and $x$ is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong — Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600°C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–200 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400°C. for a period of time of from about 6 hours to about 100 days. A more preferred temperature range is from about 150° to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230°F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000°F. for 1 hour, for example, followed by base exchange with ammonium salts followed by calcination at 1000°F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000°F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal, and characterized by an alpha value hereinafter described, are then subjected to steam treatment to reduce the activity thereof, as expressed in terms of alpha value, to less than about 500 and preferably in the range of less than about 20 but greater than zero.

The alpha value reflects the selective activity of the catalyst with respect to a high activity conventional silica-alumina cracking catalyst. To determine the alpha value, n-hexane conversion is determined and converted to a rate constant per unit volume of catalyst and compared with that of silica-alumina catalyst which is normalized to a reference activity of 1000°F. Catalytic activity of the catalysts are expressed as multiple of this standard, i.e. the silica-alumina standard. The silica-alumina reference catalyst contains about 10 weight percent $Al_2O_3$ and the remainder $SiO_2$. This method of determining alpha is more fully described in the Journal of Catalysis, Vol. IV, No. 4, August, 1965, pages 527–529.

Treatment of the zeolite with steam is carried out at a temperature of from about 250° to about 1000°C. for a period of time sufficient to effect the desired reduction in alpha. Generally, such period will be between about ½ hour and 100 hours. As above noted, a steam treating atmosphere may be employed which is 100 percent steam or steam admixed with a gas which is substantially inert with respect to the zeolite. It is contemplated that the steam treatment will generally be effected at atmospheric pressure but pressures ranging from sub-atmospheric to several hundred atmospheres may be employed. With the use of elevated pressure, temperatures in the lower region of the above specified range will usually be applicable in achieving the desired reduction in alpha value of the zeolite under treatment.

The crystallin aluminosilicate zeolites utilized herein generally have an activity, in terms of alpha, of greater than 1000 and usually within the range of 1000 and 10000. It will be realized that extent of reduction in alpha value of such zeolites will depend on the severity and duration of the steam treatment. Thus, substantially identical reduction in activity can be obtained utilizing a relatively short steam treatment under conditions of high temperature or a comparatively longer period of steam treatment at lower temperature. Illustrative of such situation is the finding that steaming of an extrudate of 65 weight percent HZSM-5 and 35 weight percent alumina for 2.5 hours at 1000°F and 1 atmosphere pressure and steaming of a second sample of such extrudate for 72 hours at 650°F and 33 atmospheres pressure both afforded a product having a reduced activity of about 200 in terms of alpha value.

Prior to use, the resulting modified zeolite is calcined in an inert atmosphere, e.g. helium or in an oxygencontaining atmosphere, e.g. air. Calcination takes place at a temperature in the approximate range of 500° to 700°C and preferably between 450° and 550°C.

In practicing the desired methylation process it may be desirable to incorporate the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

Methylation of toluene in the presence of the above-described catalyst is effected by contact of the toluene with a methylating agent, preferably methanol, at a temperature between about 300° and about 750°C and preferably between about 500° and about 700°C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. A weight hourly space velocity of between about 0.5 and about 1000 is employed. The molar ratio of methylating agent to toluene is generally between about 0.05 and about 5. When methanol is employed as the methylating agent a suitable molar ratio of methanol to toluene has been found to be approximately 0.1–2 moles of methanol per mole of toluene. With the use of other methylating agents, such as methylchloride, methylbromide, dimethylether or dimethylsulfide, the molar ratio of methylating agent to toluene may vary within the aforenoted range. Reaction is suitably accomplished utilizing a weight hourly space velocity of between about 0.5 and about 1000 and preferably between about 1 and about 100 weight of charge per weight of zeolite catalyst component per hour. The reaction product consisting predominantly of para-xylene, together with comparatively smaller amounts of meta-xylene and ortho-xylene may be separated by any suitable means, such as by passing the same through a water condenser and subsequently passing the organic phase through a column in which chromatographic separation of the xylene isomers is accomplished.

The following examples will serve to illustrate the process of this invention without limiting the same:

EXAMPLE 1

ZSM-5 crystals were obtained using the following reactants:

Silicate Solution

42.2 lb. Q-Brand Sodium Silicate (Na$_2$O/SiO$_2$ = 3.3)
52.8 lb. Water

Acid Solution

612 grams Aluminum Sulfate
1600 grams Sulfuric Acid
7190 grams Sodium Chloride
72.2 lb. Water

Organics

1290 grams Tri-n-propylamine
1110 grams n-Propylbromide

The silicate solution and acid solution were nozzle mixed to form a gelatinous precipitate that was charged to a 30 gallon stirred autoclave. When gelation was complete the organics were added and the temperature raised to 315°F. with agitation. The reaction mixture was held at 315°F. with an agitation rate of 121 RPM for 17 hours. The product at this time was analyzed by X-ray diffraction and was reported to be ZSM-5. The product was then washed free of soluble salts and dried. Analysis of the product gave the following in terms of mole ratios:

| | |
|---|---|
| Al$_2$O$_3$ | 1.0 |
| SiO$_2$ | 74.4 |
| Na$_2$O | 0.31 |
| N | 2.26 |
| C | 21.9 |

The ZSM-5 so prepared was precalcined in air at 370°C. and thereafter ammonium exchanged by contacting twice with 5N NH$_4$Cl solution at 100°C. (15 ml per gram zeolite), once for 16 hours, the second time for 4 hours, filtered, washed free of chloride and air dried.

The resulting ammonium form of ZSM-5 was converted to the hydrogen form by calcination in air at 1°C/minute to 538°C and then held at 538°C for 10 hours.

4.40 Grams of the HZSM-5 so prepared was contacted with 100 percent steam at 900°C for 16 hours. The steam treated product was found to have an alpha value of 0.12.

EXAMPLES 2–25

Toluene and methanol in molar ratios of 2:1, 1:1 and 1:2 were passed over 4.35 grams of the catalyst prepared as in Example 1 at temperatures of from 300° to 400°C at weight hourly space velocities between 1.4 and 5.8. A reaction product having a high content of xylene was obtained in each instance with selective production of para-xylene. The results are set forth in Table I below.

TABLE I

| Ex. | Temp °C. | Toluene/ Methanol | Liquid Feed ml/hr. | Grams Recovered | WHSV | Toluene Conv. % | p | Xylenes m | o | Xylene Selectivity |
|---|---|---|---|---|---|---|---|---|---|---|
| 2 | 300 | 2:1 | 15.3 | 12.6 | 2.9 | 0.5 | 41.6 | 10.0 | 48.4 | 100 |
| 3 | 350 | 2:1 | 15.3 | 12.6 | 2.9 | 2.8 | 46.3 | 16.0 | 37.7 | ~98 |
| 4 | 400 | 2:1 | 15.3 | 12.3 | 2.9 | 9.8 | 55.8 | 16.7 | 27.5 | 91 |
| 5 | 350 | 2:1 | 7.8 | 7.05 | 1.6 | 10.0 | 58.8 | 16.6 | 24.6 | ~98 |
| 6 | 350 | 2:1 | 30.0 | 25.0 | 5.8 | 0.4 | 46.6 | 20.4 | 33.0 | ~100 |
| 7 | 300 | 2:1 | 30.0 | 25.5 | 5.8 | ~0 | — | — | — | — |
| 8 | 400 | 2:1 | 30.0 | 25.2 | 5.8 | 2.2 | 52.8 | 18.0 | 29.2 | ~99 |
| 9 | 400 | 2:1 | 8.0 | 6.8 | 1.6 | >11.3 | 47.2 | 20.2 | 32.6 | 92.1 |
| 10 | 300 | 2:1 | 8.0 | 6.8 | 1.6 | 0.3 | 33.3 | 17.3 | 49.4 | ~100 |
| 11 | 300 | 1:1 | 8.0 | 6.8 | 1.6 | ~1 | ~44 | ~14 | ~42 | ~100 |
| 12 | 300 | 1:1 | 15.2 | 12.7 | 2.9 | ~.3 | ~33 | ~27 | ~40 | ~100 |
| 13 | 300 | 1:1 | 30.0 | 25.2 | 5.8 | ~0 | — | — | — | — |
| 14 | 350 | 1:1 | 11.2 | 9.2 | 2.1 | 1.8 | 49.9 | 15.8 | 34.3 | ~95 |
| 15 | 350 | 1:1 | 15.2 | 12.6 | 2.9 | 1.0 | 49.6 | 19.1 | 31.3 | ~98 |
| 16 | 350 | 1:1 | 30.0 | 24.8 | 5.8 | 0.4 | 49.0 | 24.0 | 27.0 | ~99 |
| 17 | 400 | 1:1 | 7.6 | 6.2 | 1.4 | 8.5 | 50.2 | 21.4 | 28.4 | 89.7 |
| 18 | 400 | 1:1 | 15.3 | 12.3 | 2.9 | 4.2 | ~44 | ~24 | ~32 | 93.2 |
| 19 | 400 | 1:1 | 30.4 | 25.0 | 5.8 | 1.3 | 51.2 | 19.3 | 29.5 | ~95 |
| 20 | 350 | 1:2 | 8.0 | 6.4 | 1.6 | 4.2 | 52 | 18 | 30 | 93.5 |
| 21 | 350 | 1:2 | 15.2 | 12.4 | 2.9 | 1.3 | 55.1 | 17.4 | 27.5 | ~95 |
| 22 | 350 | 1:2 | 20.0 | 16.8 | 3.9 | 0.5 | 59 | 21 | 20 | ~98 |
| 23 | 400 | 1:2 | 8.0 | 6.0 | 1.6 | 11.1 | 48.9 | 22.9 | 28.2 | 86.7 |
| 24 | 400 | 1:2 | 12.0 | 11.6 | 2.7 | 5.4 | 55.2 | 12.1 | 32.7 | 91.5 |
| 25 | 400 | 1:2 | 34.0 | 24.2 | 5.6 | 1.1 | 59.4 | 16.7 | 23.9 | ~95 |

EXAMPLES 26–32

Toluene and methanol in a molar ratio of 1:1 were passed over 2 grams of catalyst prepared in a manner similar to that of Example 1 except that steaming was carried out at 870°C for 6 hours to give an alpha value of less than 20. The catalyst was calcined at 550°C for 1 hour before each run.

Reaction of toluene and methanol was accomplished at temperatures of from 550° to 700°C at weight hourly space velocities between 11.4 and 24.2. A reaction product characterized by a high content of xylene was obtained in each instance, with selective production of para-xylene. The results are set forth in Table II below.

TABLE II

| Ex. | Temp °C. | WHSV | Conversion, % Toluene | MeOH | Xylenes p:m:o | Xylene in Aromatic Products |
|---|---|---|---|---|---|---|
| 26 | 550 | 11.8 | 15 | 75 | 63/20/17 | 88 |
| 27 | 600 | 11.4 | 25 | 79 | 66/20/15 | 86 |

TABLE II-continued

| Ex. | Temp °C. | WHSV | Conversion, % Toluene | MeOH | Xylenes p:m:o | Xylene in Aromatic Products |
|---|---|---|---|---|---|---|
| 28 | 600 | 24.1 | 15 | 73 | 68/18/14 | 90 |
| 29 | 650 | 11.8 | 36 | 90 | 67/20/13 | 86 |
| 30 | 650 | 24.1 | 23 | 78 | 72/16/11 | 89 |
| 31 | 700 | 11.8 | 44 | 95 | 70/19/11 | 86 |
| 32 | 700 | 24.2 | 33 | 95 | 77/14/9 | 85 |

From the above it will be evident that at relatively low temperatures, a severely steamed HZSM-5 catalyst yields up to about 60 percent para-xylene when a toluene-methanol mixture is passed over the catalyst (Table I). At somewhat more elevated temperatures, considerably higher yields of para-xylene were obtained over a less severely steamed catalyst (Table II). It is of interest to note that utilizing an unsteamed HZSM-5 catalyst at a temperature of 550°C, a WHSV of 8.3 employing a toluene-methanol molar feed mixture of 2:1, the xylene product obtained had a para-/meta/ortho weight ratio of 24/52/24, i.e. essentially the conventional thermodynamic equilibrium mixture.

EXAMPLE 33

Zeolite ZSM-5 was prepared by reaction of the following reactants:

Silicate Solution 90.0 lb. Q-Brand Sodium Silicate ($Na_2O/SiO_2 = 3.3$)
52.6 lb. $H_2O$
118 grams Naxad 27 dispersant (Sodium salts of polymerized substituted benzoid alkyl sulfonic acids combined with an inert organic suspending agent).

Acid Solution 1430 grams $Al_2(SO_4)_3 \cdot X\ H_2 9$ (M.W. = 595)
3440 grams $H_2SO_4$
3890 grams NaCl
54 lbs. $H_2O$

Additional Solids 2840 grams NaCl

Organics Solution 2780 grams tri-n-propylamine
2390 grams n-propyl bromide
4590 grams methyl ethyl ketone

Additional Liquid 1180 grams $H_2O$

The silicate solution and acid solution were mixed in a mixing nozzle to form a gel which was discharged into a 30 gallon autoclave to which 1180 grams of $H_2O$ had been previously added. The gel was whipped by agitation and 2840 grams of NaCl were added and thoroughly blended. The agitation was then stopped and the organics solution was added as a layer on top of the gel. The autoclave was sealed and heated to about 220°F without agitation and held there for 14–15 hours to prereact the organics. At the end of the prereaction period, the agitation was commenced at 90 RPM to start the initial crystallization period. After about 75–80 hours, the temperature was raised to 320°F and held there for about 3 hours to complete crystallization. The excess or unreacted organics were flashed off and the contents of the autoclave were cooled and discharged. The product was analyzed by X-ray diffraction and shown to be 100% crystallinity ZSM-5 based upon a standard sample. Chemical analysis of the thoroughly washed crystalline product was:

| | % Wt. | Mole Ratio |
|---|---|---|
| $Al_2O_3$ | 2.21 | 1.0 |
| $SiO_2$ | 94.9 | 72.8 |
| Na | 0.81 | — |
| $Na_2O$ | — | 0.82 |
| N | 0.67 | 2.48 |
| C | 8.2 | 35.6 |

After washing and drying at about 250°F, the zeolite was calcined in nitrogen for 3 hours at 1000°F at atmospheric pressure. The resulting product was then ion exchanged with a 1 N solution of $NH_4NO_3$ at room temperature for 1 hour using 5 cc of exchange solution per gram of dry zeolite. The ion exchanged material was washed with 4 volumes of water and dried in air at 250°F. The resulting HZSM-5 was analyzed and found to contain 0.02 weight percent sodium.

7.5 Grams of the HZSM-5 so prepared were contacted with 100 percent steam at 950°C and 1 atmosphere for 65 hours. The steam treated product was found to have an alpha of about 0.12.

Toluene and methanol in a molar ratio of 2:1 were passed over 1.1 grams of the catalyst prepared as above at a temperature of 550°C and a weight hourly space velocity of 10. Toluene conversion was 9 weight percent. The xylene content in the aromatics produced amounted to 95 weight percent. The para/meta/ortho xylene distribution, on a weight basis, was 67.9/16.2/15.9 respectively.

EXAMPLE 34

Toluene and methanol in a molar ratio of 1:1 were passed over 0.20 gram of the catalyst similar to that used in Example 33, but steamed 42 hours at 950°C, at a temperature of 600°C and a weight hourly space velocity of 25. Toluene conversion was 5 weight percent. The xylene content in the aromatics produced amounted to 94 weight percent. The para/meta/ortho xylene distribution, on a weight basis, was 97.2/1.3/1.5 respectively.

From a comparison of the results obtained in Examples 33–34, it will be evident that steaming of the HZSM-5 catalyst served to increase its selectivity for para-xylene production.

EXAMPLE 35

HZSM-5, prepared in a manner similar to that of Example 33 and having a sodium content of 0.01 weight percent, was used as the catalyst.

Toluene and methanol in a molar ratio of 1:1 were passed over 0.050 gram of such catalyst at a temperature of 550°C and a weight hourly space velocity of 100. Toluene conversion was 3 weight percent. The xylene content in the aromatics produced amounted to 87 weight percent. The para/meta/ortho xylene distribution, on a weight basis, was 55.0/20.9/24.1 respectively.

EXAMPLE 36

2.5 Grams of HZSM-5 identical to the material used in Example 35 were contacted with 100 percent steam at 950°C and 1 atmosphere for 67 hours. The steam treated product was characterized by an alpha of less than 0.1.

Toluene and methanol in a molar ratio of 2:1 were passed over 1.0 gram of the steamed HZSM-5 catalyst at a temperature of 550°C and a weight hourly space velocity of 10. Toluene conversion was 7 weight percent. The xylene content in the aromatics produced amounted to 96 weight percent. The para/meta/ortho xylene distribution, on a weight basis, was 86.2/7.3/6.5 respectively.

EXAMPLE 37

5 Grams of HZSM-5 identical to the material used in Example 36 were contacted with 100 percent steam at 950°C and 1 atmosphere for 72 hours. The steam treated product was characterized by an alpha of less than 0.1.

Toluene and methanol in a molar ratio of 1:1 were passed over 0.20 gram of the steamed HZSM-5 catalyst at a temperature of 600°C and a weight hourly space velocity of 25. Toluene conversion was 7 weight percent. The xylene content in the aromatics produced amounted to 93 weight percent. The para/meta/ortho xylene distribution, on a weight basis, was 91.2/5.2/3.6 respectively.

From a comparison of the results obtained in Examples 35-37, it will again be seen that steaming of the HZSM-5 catalyst served to increase its selectivity for para-xylene production.

What is claimed is:

1. A process for the selective production of para-xylene which comprises reacting toluene with a methylating agent in the presence of a catalyst comprising a crystalline aluminosilicate zeolite, said zeolite having a silica to alumina ratio of at least about 12 and a constraint index of from 1 to 12, which catalyst has undergone prior treatment with steam to reduce the alpha value thereof to less than about 500.

2. The process of claim 1 wherein said alpha value is within the range of less than about 20 but greater than zero.

3. The process of claim 1 wherein said methylating agent is methanol, methylchloride, methylbromide, dimethylether or dimethylsulfide.

4. The process of claim 1 wherein the step of reacting toluene with a methylating agent is carried out at a temperature between about 300° and 750°C, a pressure of between about 1 atmosphere and 1000 psig, a weight hourly space velocity between about 0.5 and about 1000 employing a molar ratio of methylating agent to toluene of between about 0.05 and about 5.

5. The process of claim 1 wherein said crystalline aluminosilicate zeolite is characterized by a silica/alumina ratio in excess of 30.

6. The process of claim 1 wherein said crystalline aluminosilicate zeolite is ZSM-5.

7. A process for the selective production of para-xylene which comprises reacting toluene with a methylating agent in the presence of a catalyst comprising a crystalline aluminosilicate zeolite, said zeolite having a silica/alumina ratio of at least about 12 and a constraint index of from 1 to 12, which catalyst has undergone prior treatment with a steam-containing atmosphere at a temperature between about 250° to about 1000°C for between about ½ hour and about 100 hours.

8. The process of claim 7 wherein said crystalline aluminosilicate zeolite is ZSM-5.

9. The process of claim 7 wherein said methylating agent is methanol.

10. The process of claim 7 wherein the step of reacting toluene with a methylating agent is carried out at a temperature between about 300° and about 750°C, a pressure of between about 1 atmosphere and 1000 psig, a weight hourly space velocity of between about 0.5 and 1000, employing a molar ratio of methylating agent to toluene of between about 0.05 and about 5.

11. The process of claim 10 wherein said temperature is between about 500° and about 700°C.

12. The process of claim 10 wherein said methylating agent is methanol present in an amount corresponding to a methanol/toluene molar ratio between about 0.1 and about 2.

* * * * *

UNITED STATES PATENT AND TRADEMARK OFFICE
CERTIFICATE OF CORRECTION

PATENT NO. : 3,965,209
DATED : June 22, 1976
INVENTOR(S) : STEPHEN A. BUTTER and LEWIS B. YOUNG It is certified that error appears in the above-identified patent and that said Letters Patent are hereby corrected as shown below:

Column 5, line 12, "11,33A" should be --11.33A--.

Column 5, line 56, "0.05 14 0.5" should be --0.05-0.5--.

Column 5, line 57, "100≅250" should be --100-250--.

Column 7, line 23, "100-200" should be --100-250--.

Signed and Sealed this

Eighteenth Day of January 1977

[SEAL]

Attest:

RUTH C. MASON
Attesting Officer

C. MARSHALL DANN
Commissioner of Patents and Trademarks